United States Patent [19]

Zielske

[11] Patent Number: 4,735,740

[45] Date of Patent: Apr. 5, 1988

[54] DIPEROXYACID PRECURSORS AND METHOD

[75] Inventor: Alfred G. Zielske, Pleasanton, Calif.

[73] Assignee: The Clorox Company, Oakland, Calif.

[21] Appl. No.: 915,133

[22] Filed: Oct. 3, 1986

[51] Int. Cl.$^4$ .................. C11D 3/39; C07C 69/017
[52] U.S. Cl. ...................... 252/95; 252/99; 252/186.38; 252/186.33; 560/142
[58] Field of Search .............. 252/95, 99, 186.38, 252/186.43; 560/142

[56] References Cited

U.S. PATENT DOCUMENTS

| | | | |
|---|---|---|---|
| 2,262,720 | 11/1941 | Earle | 514/554 |
| 2,813,896 | 11/1957 | Krimm | 260/502 |
| 2,852,495 | 9/1958 | Rocklin | 526/280 |
| 3,052,715 | 9/1962 | Rocklin | 260/488 |
| 3,706,786 | 12/1972 | Gier et al. | 560/142 |
| 3,996,152 | 12/1976 | Edwards et al. | 252/95 |
| 4,001,131 | 1/1977 | Montgomery | 252/99 |
| 4,115,058 | 9/1978 | Blumbergs et al. | 8/111 |
| 4,172,086 | 10/1979 | Berkowitz | 260/406 |
| 4,244,884 | 1/1981 | Hutchins et al. | 260/502 R |
| 4,283,301 | 8/1981 | Diehl | 252/102 |
| 4,314,949 | 2/1982 | Bettle, III et al. | 260/502 R |
| 4,337,213 | 6/1982 | Marynowski et al. | 260/502 R |
| 4,367,156 | 1/1983 | Diehl | 252/102 |
| 4,412,934 | 11/1983 | Chung et al. | 252/186.38 |
| 4,451,664 | 5/1984 | Ranade | 560/86 |
| 4,483,778 | 11/1984 | Thompson et al. | 252/94 |
| 4,486,327 | 12/1984 | Murphy et al. | 252/94 |
| 4,536,314 | 8/1985 | Hardy et al. | 252/102 |
| 4,539,130 | 9/1985 | Thompson et al. | 252/94 |
| 4,541,944 | 9/1985 | Sanderson | 252/95 |
| 4,544,503 | 10/1985 | Berry | 260/402 |
| 4,588,531 | 5/1986 | Balzer et al. | 260/402 |
| 4,681,592 | 7/1987 | Hardy et al. | 8/111 |
| 4,686,061 | 8/1987 | Nollet et al. | 252/95 |

FOREIGN PATENT DOCUMENTS

| | | |
|---|---|---|
| 0105672 | 4/1984 | European Pat. Off. |
| 0105673 | 4/1984 | European Pat. Off. |
| 0140648 | 5/1985 | European Pat. Off. |
| 0148148 | 7/1985 | European Pat. Off. |
| 0153222 | 8/1985 | European Pat. Off. |
| 0164786 | 12/1985 | European Pat. Off. |
| 0166571 | 1/1986 | European Pat. Off. |
| 864798 | 4/1961 | United Kingdom. |

OTHER PUBLICATIONS

Sorenson et al., *Preparative Methods of Polymer Chemistry*, Interscience Publishers (1968), Chap. 3, pp. 149-150.

Buehler et al., *Survey of Organic Syntheses*, Wiley-Interscience (1970), p. 816.

*Primary Examiner*—Prince E. Willis
*Attorney, Agent, or Firm*—Majestic, Gallagher, Parsons & Siebert

[57] ABSTRACT

Novel sulfonated phenyl esters of dicarboxylic acids are useful as diperoxyacid precursors in bleaching and laundering applications when combined with a source of peroxide. These diperoxyacid precursors can be produced by reacting a dicarboxylic acid, a phenol sulfonate, and a lower alkyl acid anhydride in an alkyl hydrocarbon solvent and removing a carboxylic acid byproduct through distillation. The diperoxyacid precursors have the structure:

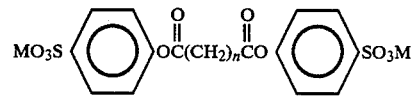

wherein n is an integer from about 4 to about 18 and M is an alkali metal, an alkaline earth metal, or ammonium. The diperoxyacid precursors have a high perhydrolysis profile coupled with a relatively low-to-moderate hydrolysis profile.

21 Claims, No Drawings

DIPEROXYACID PRECURSORS AND METHOD

FIELD OF THE INVENTION

The present invention relates to peroxyacids, and particularly to a method of synthesizing sulfonated phenyl esters of dicarboxylic acids as diperoxyacid precursors useful in bleaching and laundering applications.

BACKGROUND OF THE INVENTION

Peroxy compounds are effective bleaching agents, and compositions including diperoxyacid compounds are useful for industrial or home laundering operations. For example, U.S. Pat. No. 3,996,152, issued Dec. 7, 1976, inventors Edwards et al., discloses bleaching compositions including peroxygen compounds such as diperazelaic acid and diperisophthalic acid.

Peroxyacids have typically been prepared by the reaction of carboxylic acids with hydrogen peroxide in the presence of sulfuric acid. For example, U.S. Pat. No. 4,337,213, inventors Marynowski et al., issued June 29, 1982, discloses a method for making diperoxyacids in which a high solids throughput may be achieved.

However, granular bleaching products containing peroxyacid compounds tend to lose bleaching activity during storage, due to decomposition of the peroxyacid. The relative instability of peroxyacid presents a problem of storage stability for compositions consisting of or including peroxyacids.

One approach to the problem of reduced bleaching activity of peroxyacid compositions has been to include certain ketones which are said to activate, or catalyze, the bleaching action in peroxyacid bleaching compositions, especially at somewhat lower temperatures than about 90° C. For example, U.S. Pat. No. 4,001,131, inventor Montgomery, issued Jan. 4, 1977, discloses a bleaching composition having a water-soluble organic peroxyacid bleaching agent and a water-soluble diketone activator.

U.S. Pat. No. 4,283,301, inventor Diehl, issued Aug. 11, 1981, discloses bleaching compositions including peroxygen bleaching compounds, such as sodium perborate monohydrate or sodium perborate tetrahydrate, and activator compounds such as isopropenyl hexanoate and hexanoyl malonic acid diethyl ester. However, these bleach activators tend to yield an unpleasant odor under actual wash conditions, as discussed in U.S. Pat. Nos. 4,486,327, inventors Murphy et al., issued Dec. 4, 1984, 4,536,314, inventors Hardy et al., issued Aug. 20, 1985 and 4,539,130, inventors Thompson et al., issued Sept. 3, 1985. These patents disclose certain alpha substituted derivatives of $C_6$-$C_{18}$ carboxylic acids which are said to activate peroxygen bleaches and are said to reduce malodor.

SUMMARY OF THE INVENTION

It is an object of the present invention to provide solid, odorless diperoxyacid precursors that are water-soluble and give excellent yields of diperoxyacid when dissolved with a source of peroxide in water.

It is a further object of the present invention to provide a shelf stable, dry bleaching and/or laundering composition that gives effective peroxygen bleaching in laundering operations, even at temperatures cooler than 90° C.

Another object of the invention is to provide an economical and practical synthesis of diperoxyacid precursors useful in laundering and bleaching applications.

These and other objects are provided by the present invention.

In one aspect of the present invention, compounds are provided having the structure

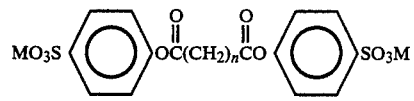

wherein n is an integer from about 4 to about 18 and M is an alkali metal, an alkaline earth metal, or ammonium.

These compounds are generally solid powders, have no odor, are water-soluble, and give excellent yields of peroxyacids upon dissolution in water with a source of peroxide such as alkaline peroxide. No odor or color is generated upon perhydrolysis. These compounds are useful precursors in forming $C_6$ to $C_{20}$ diperoxyacids (i.e., diperoxyadipic acid to diperoxyeicosanedioic acid) for bleaching and laundering applications.

In another aspect of the present invention, a method for synthesizing sulfonated phenyl esters of mono- or di-carboxylic acids is provided from an initial reaction mixture including four essential components: carboxylic acid or dicarboxylic acid, a phenol sulfonate, a lower alkyl acid anhydride, and an alkyl hydrocarbon solvent. The initial reaction mixture is heated and refluxed for a sufficient time to form an acid by-product therein. The acid by-product is removed, as by azeotropic distillation, with the azeotrope being the alkyl hydrocarbon solvent and acid by-product. Alternatively, the acid by-product may be removed by distillation where the alkyl hydrocarbon solvent acts to entrain and thus remove the acid by-product.

A sulfonated phenol ester reaction product is formed in this one pot synthesis. The inventive method is advantageous in providing high yields of the inventive diperoxyacid precursor as desired reaction product, without the necessity of a catalyst. A further advantage of the inventive method is that a single reaction vessel may be used throughout the synthesis, thus simplifying a complex organic reaction and obviating the need for transferring reactants and potentially losing product yield thereby. The desired reaction product is readily isolated, by means such as filtration, and may be simply purified. The method is practical for large-scale production.

DETAILED DESCRIPTION OF PREFERRED EMBODIMENTS

Diperoxyacids are well known and have the structure generally illustrated by Formula I, below.

Formula I

The names of diperoxyacids where n ranges from 4 to 18 (i.e., 6 to 20 total carbons in the chain) are set out for convenience below:

| n | Diperoxyacid Name |
|---|---|
| 4 | diperoxyhexanedioic acid (diperoxyadipic acid) |
| 5 | diperoxyheptanedioic acid |

| n | Diperoxyacid Name |
|---|---|
| 6 | diperoxyoctanedioic acid |
| 7 | diperoxynonanedioic acid (diperoxyazelaic acid) |
| 8 | diperoxydecanedioic acid |
| 9 | diperoxyundecanedioic acid |
| 10 | diperoxydodecanedioic acid |
| 11 | diperoxytridecanedioic acid |
| 12 | diperoxytetradecanedioic acid |
| 13 | diperoxypentadecanedioic acid |
| 14 | diperoxyhexadecanedioic acid |
| 15 | diperoxyheptadecanedioic acid |
| 16 | diperoxyoctadecanedioic acid |
| 17 | diperoxynonadecanedioic acid |
| 18 | diperoxyeicosanedioic acid |

Compounds in accordance with the invention are precursors of these diperoxyacids, and have the structure illustrated by Formula II, below.

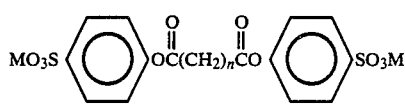

Formula II wherein n is an integer from about 4 to about 18 and M is an alkali metal, an alkaline earth metal, or ammonium.

These inventive compounds (illustrated by Formula II) are precursors of the Formula I diperoxyacids via a reaction mechanism that will be more fully described hereinafter. The inventive diperoxyacid precursors are conveniently synthesized by means of a novel method for synthesizing sulfonated phenyl esters, as will now be described.

The method requires four essential components in an initial reaction mixture. These are: a monocarboxylic acid or a dicarboxylic acid, a phenol sulfonate, a lower alkyl acid anhydride, and an alkyl hydrocarbon solvent. These four essential components form a two-phase initial reaction mixture. One phase of the initial reaction mixture is solid (the phenol sulfonate). The monocarboxylic acid or dicarboxylic acid and lower alkyl acid anhydride are dissolved or suspended as a melt of fine droplets in the alkyl hydrocarbon solvent to constitute a liquid phase.

Either monocarboxylic acid or dicarboxylic acids may be chosen as feed stock for the initial reaction mixture; however $C_6$-$C_{20}$ dicarboxylic acids are preferred because they result in the sulfonated phenol ester reaction products illustrated by Formula II.

The sulfonate group is para to the hydroxyl group of the phenol sulfonate and has an alkali metal, such as sodium or potassium, an alkaline earth metal, such as calcium or magnesium, or an ammonium radical. Sodium phenol sulfonate is preferred due to its ready commercial availability.

Lower alkyl acid anhydrides suitable for use in the inventive method include acetic anhydride, propionic anhydride, and butyric anhydride. Acetic anhydride is preferred, due to ready availability and low cost.

As will be more fully described hereinafter, practice of the method produces a carboxylic acid by-product. This by-product corresponds to the lower alkyl acid anhydride utilized in the initial reaction mixture. That is, if acetic anhydride is used as the lower alkyl acid anhydride component in the initial reaction mixture, then acetic acid will be a by-product.

It is necessary in practicing this invention to remove the carboxylic acid by-product during formation of the desired reaction product from the initial reaction mixture. The carboxylic acid by-product is preferably removed as an azeotrope by azeotropic distillation or as an entrained vapor. The azeotrope is the carboxylic acid by-product together with the alkyl hydrocarbon solvent. Thus, the particular hydrocarbon solvent is chosen for its ability to form such an azeotrope or to entrain (codistill) the acid by-product.

Suitable hydrocarbon solvents include heptane, octane, nonane, decane, undecane, dodecane, tridecane, and mixtures thereof. Water insoluble isoparaffinic solvents are also suitable as the alkyl hydrocarbon solvent, such as is commercially available from Exxon Corporation under the same "Iso-Par".

The overall reaction, from initial reaction mixture to formation of desired sulfonated phenyl reaction product, is generally illustrated by Reaction Scheme I, below, where dicarboxylic acid is illustrated as being in the initial reaction mixture and $R_1$ is methyl, ethyl, or propyl.

REACTION SCHEME I

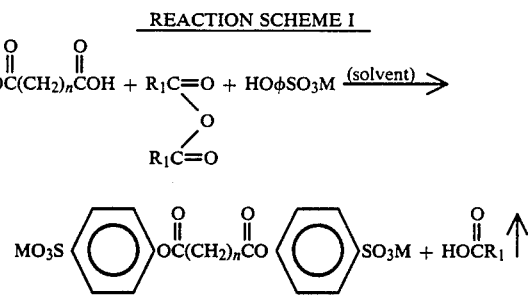

While the stoichiometric amount of dicarboxylic acid:phenol sulfonate:lower alkyl acid anhydride is 1:2:2 in the inventive method, when dicarboxylic acid is chosen (as illustrated by Reaction Scheme I), it has been found that a molar excess over stoichiometric levels for the lower alkyl acid anhydride and the phenol sulfonate are preferred to achieve high yields. For example, moderate excesses of the phenol sulfonate and the lower alkyl acid anhydride components, on the order, for example, of about 12-15% over stoichiometric levels, are most preferred.

The initial reaction mixture is heated and refluxed for a sufficient time to form an intermediate reaction mixture which has the carboxylic acid by-product therein, then followed by removal of the carboxylic acid by-product. This reflux time is necessary because it is believed that the reaction mechanism illustrated by Reaction Scheme I proceeds via an intermediate lower alkyl ester which is formed by means of nucleophilic attack of the phenol sulfonate on the lower alkyl acid anhydride. It has been found that little or no reflux time results in lower yields of the desired sulfonated phenyl ester reaction product. Sufficient reflux time in which to form the intermediate lower alkyl ester and the carboxylic acid by-product is at least about 2 hrs., more preferably about 4 hrs. to about 6 hrs. Longer reflux times have been found to result in only small, additional increases in yields.

The initial reaction mixture is heated to a temperature of at least about 150° C., more preferably at least about 170° C., and most preferably is conducted at about 200°-215° C. Below temperatures of about 150° C., yields are low. Temperatures should not exceed 300° C., and preferably will not exceed about 250° C. to about 270° C. Excessive temperatures can lead to loss of the lower alkyl acid anhydride by flash-off and charring of components.

Removal of the carboxylic acid by-product is believed to drive the reaction by means of nucleophilic attack of the dicarboxylic acid on the intermediate lower alkyl ester to form a mixed anhydride, which in turn reacts with the phenol sulfonate and results in the desired sulfonated phenol ester reaction product. Removing the carboxylic acid by-product following the refluxing results in good yields of the desired reaction product.

This removal is preferably achieved by distillation. The carboxylic acid by-product azeotropes with or is entrained by the alkyl hydrocarbon solvent. Initial fractions are very rich in the carboxylic acid by-product. The distillate (and internal temperature) are preferably monitored so that when the internal temperature rises to that of the pure alkyl hydrocarbon solvent and the lower layer (containing acid by-product) of distillate remains constant, when the distillation is stopped.

The desired sulfonated phenyl ester reaction product is a suspended solid at the end of the reaction. This crude reaction product may be readily isolated, by means such as filtration. The crude reaction product may thereafter be purified, by means such as recrystallization.

Where the initial reaction mixture includes a dicarboxylic acid, then the reaction product has the structure illustrated by Formula II.

Thus, the inventive method is preferably practiced to synthesize the inventive diperoxyacid precursors in good yields.

The diperoxyacid precursors are usefully formulated with a solid source of peroxide, such as an alkaline peroxide, in an amount effective to perhydrolyze at least most of the diperoxyacid precursor, and thus to provide effective bleaching. Suitable sources of peroxide include sodium perborate monohydrate, sodium perborate tetrahydrate, sodium carbonate peroxyhydrate, sodium pyrophosphate peroxyhydrate, urea peroxyhydrate, sodium peroxide, and mixtures thereof. Sodium perborate monohydrate and sodium perborate tetrahydrate are particularly preferred alkaline peroxides for combination with the diperoxyacid precursors as a dry bleach composition or, when surfactant is included, as a dry laundering and bleaching composition.

The source of peroxide (that is, compounds yielding hydrogen peroxide in an aqueous solution) itself constitutes a peroxygen bleaching compound. However, the dry bleach composition including diperoxyacid precursor and peroxide source together provide better bleaching, particularly at temperatures below about 60° C., than the peroxide source alone. The range of peroxide to diperoxyacid precursor is preferably determined as a molar ratio of peroxide to ester groups contained in the precursor. Thus, with diester precursors, the range of peroxide to each ester group is a molar ratio of from about 1 to 10, more preferably about 2 to 5.

When the bleaching compositions are also laundering compositions (that is, include surfactant), then it is preferred that the amount of peroxygen bleach composition be from about 1 wt. % to about 20 wt. % of the dry laundering composition, and preferably from about 5 wt. % to about 10 wt. %.

The peroxygen bleach composition (including a diperoxyacid precursor and a source of peroxide) may be formulated with a wide variety of different surfactants, and the well known dry anionic, cationic, non-ionic, ampholytic or zwitterionic surfactants, or mixtures of such surfactants, are suitable. A few examples are described below.

Useful anionic surfactants include, for example, the water-soluble salts (e.g., alkali metal, ammonium and alkyl ammonium salts) of organic sulfuric reaction product having in their molecular structure an alkyl group containing from about 10 to about 20 carbon atoms and a sulfonic acid or sulfuric acid ester group, such as the sodium and potassium alkyl sulfates and the alkyl benzene sulfonates.

Suitable nonionic surfactant for use in a dry laundering composition of the invention include the polyethylene oxide condensates of alkyl phenols, the condensation products of aliphatic alcohols with from about 1 to about 25 moles of ethylene oxide, and the like.

Suitable zwitterionic surfactants include derivatives of secondary and tertiary amines, derivatives of heterocyclic secondary and tertiary amines, or derivatives of quaternary ammonium, quaternary phosphonium or tertiary sulfonium compounds.

Useful cationic surfactants include the alkyl quaternary ammonium surfactants.

The dry bleach compositions and dry laundering compositions in accordance with the invention may also include one or more laundry adjuvants such as detergent builders, buffering agents, enzymes, and minor amounts of other water-soluble solid materials such as wetting agents, dyes and perfumes.

Buffering agents can be utilized to maintain an alkaline pH of the bleaching and/or laundering solutions, since the peroxygen bleach composition of the invention is most effective at a pH of about 9.0 to about 10.5.

At a pH of either 9.5 or 10.5, a temperature of 21° C., and a 4:1 mole ratio of peroxide to diperoxyacid precursor (that is, a 2:1 mole ratio of peroxide to each ester group) results in a perhydrolysis of about 86%, at pH 10.5, and at a temperature of 30° C. results in a perhydrolysis of about 94%. This desirably high perhydrolysis is coupled with a desirably low-to-moderate hydrolysis profile. Thus, the inventive diperoxyacid precursors will preferentially form the diperoxyacid when dissolved in water.

Examples IA–IC illustrate use of the inventive method to prepare three diperoxyacid precursor embodiments of the invention ($C_6$, $C_9$ and $C_{12}$ respectively).

EXAMPLE IA

A 2 liter three-neck Morton flask was equipped with a paddle stirrer, condenser with drying tube, and a heating mantle. The dodecane (600 ml, b.p. 215° C.) was added to the flask and heated to about 165° C. To this was added the adipic acid (40.9 g., 280 mmole, m.p.=152° C.) with strong stirring. When this acid had all melted anhydrous p-phenolsulfate (118.5 g, 600 mmole) was added followed by acetic anhydride (57 ml, 600 mmole) and sodium acetate (1.8 g, 20 mmole).

This mixture was kept at about 165° C. with rapid stirring for 4 hours. At the end of this time, a Dean-Stark trap was added between the reaction flask and condensation and a thermometer was added to the reaction pot. The acetic acid was removed over the next 3 hours via the Dean-Stark trap. The initial internal temperature was 131° C. when distillate began to appear in the Dean-Stark trap and rose to 215° C. at the end of 3 hours.

The reaction mixture was allowed to cool and then filtered to give to a tan solid. The solid was washed with acetone (2×700 ml), filtered, and air dried in the hood to give 147.5 g of crude product. This crude product was analyzed for 71.0% diester and thus the yield of diester in the reaction was 75%.

A portion (135.0 g) of the crude product was dissolved in hot methanol-water (50/50 v/v, 675 ml) to give a dirty yellow-colored solution. The hot solution was filtered to give a light gold-yellow solution. This was cooled in an ice-bath to 5° C., with stirring. Filtration of the resulting slurry gave a white solid, which then dried in the vacuum oven (110° C., 6 hours), gave 64.0 g of product.

The infrared spectrum of the dried solid gave a large ester peak at 1755 cm$^{-1}$. Analysis of the recrystallized solid by HPLC (external standards) gave 92.2% diester and 4.1% phenolsulfate. The 13 C-nmr (D$_2$O) gave: 177.1 ppm (ester carbonyl), 154.8 (aromatic attached to oxygen), 143.6 (aromatic attached to sulfur), 130.1 (aromatic ortho to sulfur), 124.8 (aromatic ortho to oxygen), 36.1 (methylene carbon alpha to carbonyl), 26.2 (methylene carbon beta to carbonyl).

EXAMPLE IB

A 500 ml three-neck Morton flask was equipped with paddle stirrer, condenser with drying tube and a heating mantle. To this was added dodecane which was heated to about 160° C. The azelaic acid (11.75 g, 62.5 mmole, m.p. 110° C.) was added with rapid stirring. When it had all melted, the acetic anhydride (13.5 ml, 143 mmole) was added followed by anhydrous sodium p-phenolsulfate (27.5 g, 140 mmole) and sodium acetate (0.41 g, 5 mmole).

This mixture was stirred rapidly at this same temperature for 22 hours. At the end of this time a Dean-Stark trap was added between the reaction flask and condenser and a thermometer was added to the flask. The acetic acid was removed over the next 6 hours. The initial temperature was 139° C. when distillate began to appear in the Dean-Stark trap and rose to 215° C. at the end of 6 hours.

The reaction mixture was allowed to cool and was filtered to give a tan solid. The solid was washed with acetone (2×500 ml), filtered and air dried to give 37.6 g of crude solid. This crude product was analyzed for 78.6% diester (HPLC) and thus the yield of diester in the reaction was 87%. The infrared spectrum showed a larger ester peak at 1755 cm$^{-1}$.

In an analogous manner, a large sample of crude (71.9%, diester) azelaic acid precursor was prepared. A sample (164.0 g) of this crude was dissolved in hot methanol-water (50/50 v/v, 650 ml) to give a yellow solution and this was cooled in an ice bath to 5° C., then filtered to give a whitish solid. The solid was washed with acetone (2×600 ml), filtered, air dried, and finally dried in a vacuum oven (110° C., overnight). The dried solid amounted to 100.2 g of a cream colored solid which showed a strong ester band (1755 cm$^{-1}$) in the infrared spectrum. The HPLC (external standard) gave 94.8% diester for this purified solid. The 13 C-nmr (D$_2$O) showed: 176.9 ppm (ester carbonyl), 155.5 (aromatic attached to oxygen), 144.9 (aromatic attached to sulfur), 130.9 (aromatics ortho to sulfur), 125.1 (aromatics ortho to oxygen), 37.4 (methylene carbon alpha to carbonyl), 27.8 (methylene carbon beta to carbonyl) and 31.7 (remainder of internal methylene carbons).

EXAMPLE IC

A three-neck Morton flask (500 ml) was equipped with a paddle stirrer and condenser with drying tube. Into this flask was added dodecane as the alkyl hydrocarbon solvent, which was heated to 150°-160° C. in an oil bath. Solid dodecanedioic acid (14.4 g, 62.5 mmole, m.p. 140° C.) was added and stirred until melted and a cloudy mixture formed. Anhydrous sodium phenol sulfonate (27.0 g, 138 mmole) acetic anhydride (13.5 ml, 143 mmole), and sodium acetate (0.41 g, 5 mmole) were added to the melted dodecanedioic acid. This initial reaction mixture was refluxed for 3.5 hours, and then a Dean Stark trap and thermometer were added to the apparatus. The temperature of the oil bath was raised to 235° C. and the internal temperature and volume of distillate was monitored.

Acetic acid by-product formed in the reaction mixture and distilled with the dodecane solvent. Both the internal temperature and the volume of distillate were monitored. When the internal temperature rose to that of the pure hydrocarbon solvent (215° C.) and the volume of distillate remained constant (about 23 hrs.), then the distillation was stopped. The reaction mixture was cooled and the reaction product removed by filtering. The reaction product (a tan solid) was washed with acetone and dried. Yield was 38.4 g (83%).

The crude reaction product was characterized by IR, HPLC and $^{13}$C-NMR (D$_2$O). An IR of the solid gave a strong aromatic ester band at 1755 cm$^{-1}$ and showed a very small OH band at about 3500 cm$^{-1}$. HPLC analysis of the product gave 78.8% diester, 4.2 monoester, 10.3% acetate ester, and 3.7% phenol sulfonate. Thus, the total amount of diester present in the crude product was 30.3 g, or 51.7 mmole of diester and a yield of 83%. $^{13}$ C-NMR (D$_2$O): 175.6 ppm (ester carbonyl), 154.5 (aromatic attached to oxygen), 143.8 (aromatic attached to sulfur), 129.8 (aromatics ortho to sulfur), 124.1 (aromatics ortho oxygen), 36.4 (methylene carbon $\alpha$ to carbonyl), 31.3 (interior methylene carbons), 26.9 (methylene carbon $\beta$ to carbonyl).

In an analogous procedure, another sample of crude diperoxy-dodecanoic acid precursor was prepared and 160 g of this crude diester (67.4 wt. % diester) was added to hot H$_2$O-MeOH (50/50 v/v, 800 ml). The slurry was stirred until all solid had dissolved and was then cooled in an ice bath until the internal temperature was 5° C. The resulting thick slurry was filtered, the solid on the filter pad was washed with acetone (2×600 ml), filtered and air dried. The solid was finally dried in a vacuum oven (110° C.) overnight. The purified dried solid, 98.9 g, was found to be 97.3% diester by HPLC (external standard) analysis.

EXAMPLE II

A preparation of diperoxyazelaic acid precursor was conducted in an analogous manner, as described by Example IC, but without any basic catalyst (that is, no sodium acetate).

A 2 liter three-neck Morton flask was equipped with paddle stirrer, condenser with drying tube, and heating mantle. To this was added Isopar M (b.p. 207° C., 550 ml) and this heated to about 150° C. The azelaic acid (52.6 g. 280 mmole, m.p. 110° C.) was added and when it all melted the acetic anhydride (61. 4 l, 650 mmole) was added followed by anhydrous sodium p-phenolsulfonate (116 g, 592 mmole).

This mixture was kept at about 165° C. for 4.5 hours. Then a Dean-Stark trap was placed between the reaction flask and condenser and a thermometer was added to the flask. The acetic acid was removed over the next 3½ hours. The internal temperature was 133° C. when distillate began to appear in the Dean-Stark trap and rose to about 210° C. at the end of 3½ hours.

The reaction mixture was cooled and then filtered to give a dark tan solid. (The color was darker than that obtained from reaction when sodium acetate catalyst was used). The solid was washed with acetone (2×700 ml), filtered and air dried over the weekend. The solid gave 155.8 g of material that had a very strong ester band at 1760 cm$^{-1}$ in the infrared. The HPLC analysis (external standard) showed 72.3% diester present.

A batch of the above solid (140.0 g) was added to hot methanol-water (50/50 v/v, 525 ml) to give a dark brown solution. This was cooled in an ice bath to 5° C. and the resulting slurry filtered to give a light tan solid. This solid was washed in acetone (2×600 ml), filtered, air dried, and finally dried in a vacuum oven (110° C., overnight). The resulting solid (89.0 g) gave a strong ester ban at 1760 cm$^{-1}$ in the infrared and HPLC analysis (external standard) gave 100% diester.

The yields of resultant desired reaction product (both crude and purified) were comparable to the yields described in Example IC. However, the crude product produced was a darker tan color than that made with catalyst present.

Additional runs were undertaken with an acidic catalyst (methane sulfonic acid). A fair amount of product was formed at 151° C. with 8% methane sulfonic acid as catalyst, but the product was darker tan than that produced with the basic catalyst. At temperatures of 174° C. (decane as solvent), and at 215° C. (dodecane as solvent), the product was quite dark.

Tables I, II and III illustrate temperature and time effects on yield for the three groups of initial reaction mixtures. The initial reaction mixtures for which the Table I data is illustrated included sodium acetate as basic catalyst and had a 12–14% molar excess of the acid anhydride and phenol sulfonate components over stoichiometric levels. The initial reaction mixtures from which the Table II data was taken was similar but had methane sulfonic acid as acidic catalyst. The initial reaction mixture from which the Table III data came had no catalyst, and had a 12–14% molar excess of the phenol sulfonate and the acid anhydride components. The acid anhydride used for all three groups was acetic anhydride. The diester reaction product of the first and second groups (Tables I and II) was di-(sodium p-phenylsulfonate)-dodecanedioate.

TABLE I

| Run # | Solvent | Solvent b.p. (°C.) | Reflux Time (hrs.) | Distillation Time (hrs.) | % Yield of Diester |
|---|---|---|---|---|---|
| 1 | nonane | 151 | 4.5 | 21 | 19 |
| 2 | decane | 174 | 4.5 | 26 | 58 |
| 3 | dodecane | 215 | 2 | 2 | 62 |

TABLE I-continued

| Run # | Solvent | Solvent b.p. (°C.) | Reflux Time (hrs.) | Distillation Time (hrs.) | % Yield of Diester |
|---|---|---|---|---|---|
| 4 | dodecane | 215 | 2 | 12 | 73 |
| 5 | dodecane | 215 | 4.5 | 4 | 79 |
| 6 | dodecane | 215 | 3.5 | 23 | 78 |

As can be seen from Table I, the yield dropped off considerably at temperatures below about 174° C. with basic catalyst.

TABLE II

| Run # | Solvent | Solvent b.p. (°C.) | Reflux Time (hrs.) | Distillation Time (hrs.) | % Yield of Diester |
|---|---|---|---|---|---|
| 7 | nonane | 151 | 2 | 9 | 50 |
| 8 | nonane | 151 | 3 | 26.5 | 57 |
| 9 | decane | 174 | 2 | 6 | 35 |
| 10 | dodecane | 215 | 2 | 2.5 | 41 |

As can be seen from Table II, the yield decreased at temperatures above about 151° C. with acidic catalyst.

TABLE III

| Run # | Parent Acid | Solvent | B. P. | Distillation Time (hrs.) | % Yield of Ester |
|---|---|---|---|---|---|
| 11 | Azelaic | Dodecane | 215° C. | 3.5 | 75 |

Table III illustrates practice of the invention with no catalyst. Run 11 yielded di-(sodium p-phenylsulfonate)-azelate.

Table IV, below, illustrates some effects of reflux time variations and amounts of the phenol sulfonate and the acid anhydride components. Runs 12–16 were conducted with 8% basic catalyst (sodium acetate), and run 17 with no catalyst. The diester reaction product was di-(sodium p-phenolsulfonate)-azelate.

TABLE IV

| Run # | % Reagent Molar Excess over Stoichiometric | | Reflux Time (hrs.) | Distillation Time (hrs.) | % Yield of Diester |
|---|---|---|---|---|---|
| | Acetic Anhydride | p-Phenol Sulfonate | | | |
| 12 | 14 | 12 | 4.5 | 4 | 84 |
| 13 | 14 | 12 | 22 | 6 | 87 |
| 14 | 20 | 0 | 5 | 4 | 68 |
| 15 | 5 | 0 | 5 | 4 | 60 |
| 16 | 16 | 6 | 4.5 | 4 | 75 |
| 17 | 16 | 6 | 4.5 | 3.5 | 75 |

Table V, below, summarizes the data obtained from purification of crude phenol sulfonate diester of azelaic acid by recrystallization with different solvent systems. Use of the water-methanol solvent system gave a very high purity product. Small amounts of phenol sulfonate (about 3%) and even smaller amounts of monoester and acetate ester (about 0.5% each) were generally present in the recrystallized diester reaction product, which was di-(sodium p-phenylsulfonate-azelate).

TABLE V

| Crude* Composition % Diester | Solvent Composition 50—50, v:v | Ratio (v:wt) Solvent:Crude | Recrystallized Product* % Diester | Diester Recovered from Crude, % |
|---|---|---|---|---|
| 67 | H$_2$O—MEOH | 5:1 | 97 | 89 |
| 73 | H$_2$O—MEOH | 4:1 | 100 | 87 |
| 72 | H$_2$O—MEOH | 3.7:1 | 100 | 88 |

TABLE V-continued

| Crude* Composition % Diester | Solvent Composition 50—50, v:v | Ratio (v:wt) Solvent:Crude | Recrystallized Product* % Diester | Diester Recovered from Crude, % |
|---|---|---|---|---|
| 70 | H₂O—iPrOH | 3.7:1 | 93 | 78 |
| 70 | H₂O—ETOH | 3.7:1 | 97 | 84 |
| 71 | H₂O—ACETONE | 6.6:1 | 100 | 65 |

*Analysis done via HPLC using external standard.

The inventive method may be practiced with a monocarboxylic acid in the initial reaction mixture in order to prepare high yields of monoesters of p-phenolsulfonate easily in a one-pot synthesis. Thus, the inventive method was used to prepare a variety of different monoesters, as illustrated by Table VI, below.

TABLE VI

| Monoesters Prepared | Reflux (Hrs.) | Disillation (Hrs.) | Solvent | Catalyst | Yield |
|---|---|---|---|---|---|
| CH₃(CH₂)₆CO—⌬—SO₃Na | 3.5 | 23 | dodecane | NaOAc | 78% |
| CH₃(CH₂)₇CO—⌬—SO₃Na | 4 | 3 | dodecane | NaOAc | 76% |

Practice of the inventive method provides peroxyacid precursors yielding good to excellent perhydrolysis profiles of mono- or di-peroxyacids. Thus, the following seven peroxyacid precursors were prepared and then dissolved in a 0.02M carbonate buffer, pH 10.5, 21° C., in a 1:2 ratio peroxide source to ester group, and tested for yield of peroxyacid after 5 minutes. Each solution was calculated as providing a theoretical 14 ppm A.O. The results are set out in Table VII.

TABLE VII

| Structure | Perhydrolysis Yield of Peracid pH 10.5 |
|---|---|
| CH₃(CH₂)₆CO—⌬—SO₃Na | 75% |
| CH₃(CH₂)₇CO—⌬—SO₃Na | 86% |
| CH₃(CH₂)₃CH(C₂H₅)—CO—⌬—SO₃Na | 54% |
| (CH₃)₃C—CH₂CH(CH₃)CH₂CO—⌬—SO₃Na | 86% |
| NaO₃S—⌬—OC(CH₂)₄CO—⌬—SO₃Na | 91% |

TABLE VII-continued

| Structure | Perhydrolysis Yield of Peracid pH 10.5 |
|---|---|
| NaO₃S—⌬—OC(CH₂)₇CO—⌬—SO₃Na | 83% |

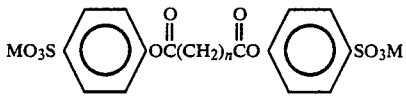

86%

Although the various aspects of the present invention have been described with respect to a preferred embodiment thereof, it will be understood that the invention is entitled to protection within the full scope of the appended claims.

I claim:

1. A diperoxyacid precursor compound having the structure

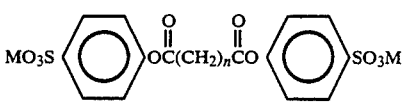

wherein n is an integer from about 4 to about 18 and M is an alkali metal, an alkaline earth metal, or ammonium.

2. The compound as in claim 1 wherein n is 5 or 8.
3. The compound as in claim 2 wherein M is sodium.
4. A dry bleach composition comprising: a diperoxyacid precursor and a source of peroxide, the diperoxyacid precursor having the structure $$MO_3S-\bigcirc-OC(CH_2)_nCO-\bigcirc-SO_3M$$

wherein n is an integer from about 4 to about 18 and M is an alkali metal, an alkaline earth metal, or ammonium, the source of peroxide in an amount effective to perhydrolyze at least most of the diperoxyacid precursor in the presence of an aqueous solution at a pH of at least about 9.0 and at a temperature of at least about 21° C.

5. The compound as in claim 4 wherein the source of peroxide includes sodium perborate monohydrate, sodium perborate tetrahydrate, sodium carbonate peroxyhydrate, sodium pyrophosphate peroxyhydrate, urea peroxyhydrate, sodium peroxide, and mixtures thereof.

6. The bleach composition as in claim 4 or 5 wherein a diperoxyacid forms from the diperoxyacid precursor as a result of perhydrolysis thereof.

7. A dry laundering composition comprising:
   an anionic, cationic, non-ionic, ampholytic or zwitterionic surfactant, or mixtures thereof; and
   a peroxygen bleach composition in an amount from about 1 wt. % to about 20 wt. % of the dry laundering composition, the peroxygen bleach composition including a diperoxyacid precursor and an alkaline peroxide, the diperoxyacid precursor having two ester moieties, the alkaline peroxide being in a mole ratio with respect to each ester moiety of the diperoxyacid precursor of at least about 2:1, the diperoxyacid precursor having the structure $$MO_3S-\phi-OC(CH_2)_nCO-\phi-SO_3M$$

wherein n is an integer from about 4 to about 18 and M is an alkali metal, an alkaline earth metal, or ammonium.

8. The dry laundering composition as in claim 7 further comprising a laundry adjuvant, the laundry adjuvant including one or more of a detergent builder, a buffer, an enzyme, a wetting agent, a dye or a perfume.

9. A method for synthesizing sulfonated phenyl esters comprising:
   providing an initial reaction mixture including a carboxylic acid or a dicarboxylic acid, a phenol sulfonate, a lower alkyl acid anhydride, and an alkyl hydrocarbon solvent, the phenol sulfonate and the lower alkyl acid anhydride each being in a molar ratio with respect to the dicarboxylic acid of at least about 2:1 or with respect to the carboxylic acid of at least about 1:1;
   heating the initial reaction mixture to a temperature between about 150° C. to about 300° C. and refluxing the heated reaction mixture for at least two hours to form an intermediate reaction mixture having a carboxylic acid by-product therein; and
   removing the carboxylic acid by-product as a distillate with the alkyl hydrocarbon solvent from the intermediate reaction mixture to form a subsequent mixture, said subsequent mixture including a sulfonated phenyl ester reaction product.

10. The method as in claim 9 wherein the dicarboxylic acid has the structure $$HOC(CH_2)_nCOH$$

wherein n is an integer from about 4 to about 18, and the heating of the initial reaction mixture is to a temperature of between about 150° C. to about 270° C.

11. The method as in claim 9 or 10 wherein the phenol sulfonate has the structure $$HO\phi SO_3M$$

and M is an alkali metal, an alkaline earth metal, or ammonium.

12. The method as in claim 9 or 10 wherein the lower alkyl acid anhydride is acetic anhydride, propionic anhydride or butyric anhydride.

13. The method as in claim 9 or 10 wherein the lower alkyl acid anhydride is acetic anhydride.

14. The method as in claim 9 or 10 wherein the alkyl hydrocarbon solvent is hectane, octane, nonane, decane, undecane, dodecane, tridecane, mixtures thereof, or water insoluble isoparaffinic solvents.

15. The method as in claim 9 or 10 wherein the heating is at a temperature of about 200° to about 215° C.

16. The method as in claim 9 wherein the initial and the intermediate reaction mixture each has a solid and a liquid phase.

17. The method as in claim 10 wherein the sulfonated phenyl ester reaction product has the structure $$MO_3S-\phi-OC(CH_2)_nCO-\phi-SO_3M$$

wherein n is an integer from about 4 to about 18 and M is an alkali metal, an alkaline earth metal, or ammonium.

18. The method as in claim 17 further comprising:
   isolating the reaction product following removal of substantially all acid by-product.

19. The method as in claim 18 wherein the reaction product is isolated by filtration and is thereafter purified by recrystallization.

20. The method as in claim 10 wherein the phenol sulfonate and the lower alkyl acid anhydride of the initial reaction are each in a molar ratio with respect to the dicarboxylic acid of greater than about 2:1.

21. The method as in claim 9 wherein the initial reaction mixture includes an acidic or basic catalyst.

* * * * *